United States Patent [19]

Szatlóczky et al.

[11] Patent Number: 4,622,341

[45] Date of Patent: Nov. 11, 1986

[54] GROWTH-PROMOTER FODDERS AND FEED ADDITIVES AND PROCESS FOR THEIR PREPARATION

[75] Inventors: Ernö Szatlóczky; Ákos Andor; András Vucskits, all of Budapest; Géza Márai, Gödöllö ; Erzsebet Palágyi nee Vajdovics, Budapest, all of Hungary

[73] Assignee: Novotrade RT, Budapest, Hungary

[21] Appl. No.: 599,465

[22] Filed: Apr. 12, 1984

[30] Foreign Application Priority Data

Apr. 14, 1983 [HU] Hungary ............................. 1305/83

[51] Int. Cl.$^4$ ........................................... A61K 31/135
[52] U.S. Cl. .................................................... 514/648
[58] Field of Search ........................................ 514/648

[56] References Cited

PUBLICATIONS

Drugs for Heart Disease, edited by John Hamer, pub. by Chapman and Hall (1979) pp. 485–487—"Drugs".

*Primary Examiner*—Frederick E. Waddell
*Attorney, Agent, or Firm*—Keil & Weinkauf

[57] ABSTRACT

The invention relates to growth-promoter fodders or feed additives, comprising as active ingredient 0.002 to 98% by weight of prenylamine or a salt thereof, suitable for feeding purposes, in admixture with 99.988 to 2% by weight of an inert fodder carrier and optionally with further feed additives.

The growth promoting fodders and feed additives of the present invention provide high weight gain, good fodder utilization and do not cause resistance or cross-resistance.

6 Claims, No Drawings

GROWTH-PROMOTER FODDERS AND FEED ADDITIVES AND PROCESS FOR THEIR PREPARATION

This invention relates to growth-promoter (weight-gain increasing) fodders and feed additives and a process for the preparation thereof.

It is known that as a result of the extremely rapid development of industrial-scale animal husbandry the keeping and feeding of animals is encountered with several difficulties. The large animal population, the small available space, the anti-natural breeding conditions, the lack in natural fodders and the various animals diseases require the use of special feed additives restoring the modified biological function and enabling the intensive production of animal products despite of the above difficulties.

The feed additives satisfy the requirements of micro elements, macro elements, vitamins, flavour and aroma substances etc. of animals kept and fed under intensive conditions. The said feed additives do not ensure, however, the weight gain required by the constantly developing food industry.

In order to achieve the desired weight gain additives are used which exhibit the most preferable effect on the biological functions of animals under the modified conditions of intensive animal breeding. According to F. Okermann and R. I. Moermans coccidiosis can be eliminated under the conditions of industrial-scale broiler breeding by addition of the antibiotic Salynomycin (Rijkstation voer Kleinveetset, Manual 1981).

According to Schneider olaquindox (Bayo-Nox; 2-[N-(2-hydroxyethyl)-carbamoyl]-3-methyl-quinoxaline-1,4-dioxide) significantly increases the resistance of young piglets against dysentery, it increases weight-gain and improves fodder utilization (D. Schneider: Data on Effect of Bayo-Nox in Swine in the Federal Republic of Germany, Bayo-Nox Symposium Düsseldorf, 25th February 1977, page 23).

According to Hoefer, Harmon and Leucke [J. Animal Sci. 20, 936 (1981)] the antibiotics Virginiamycin and Spiramycin exert a favourable effect on the intestinal flora of artificially fed and early separated piglets.

According to Prinz [Der praktische Tierarzt 53, 282 (1972)] the composition Ralgro (dihydroxy-undecyl-$\beta$-resorcinol-lacton) possesses a significant weight-gain increasing effect.

Growth promoters are to be used in cases in which— for the reasons stated above—natural fodders or nutriments are not utilized at a suitable rate and the physiological and microbiological conditions are influenced in an unfavourable, adverse manner.

Antibiotics, chemotherapeutical agents and antimicrobial compositions are the most well-known and wide-spreadly used growth promoters. Their application is based on the recognition that drugs used in veterinary therapy can enhance weight gain, generally if added in higher doses. According to Feed Additive Compendium published in the United States (1982, pages 171–172) coccidiosis and the treatment and prophylaxis of various diseases caused by bacteria are mentioned as field of indication of Flavomycin, Virginiamycin and Spyramicin, but it is also disclosed that the said compositions are suitable for the increase of daily weight gain and improvement of fodder utilization of animals kept under industrial scale conditions.

The common disadvantage of known growth promoters also used in therapy resides in the residues, resistance, toxicity, cancerogenic and teratogenous effect. For this reason according to principles internationally accepted in animal husbandry and the consumption of animal products the use of such compositions as growth promoter is to be avoided (Swann Committee Report on the Use of Antibiotics in Animal Husbandry and Veterinay Medicine, 1969, CMND 4190, HMSO, London). According to Swann it is dangerous to use antibiotics applied in human therapy as feed additive because the said antibiotics get into the flesh of animals and may cause resistance and allergic symptoms as human nutrients. Moreover, in the veterinary science it is not recommended to use antibiotics simultaneously for therapeutic and prophylactic purposes because of the risk of resistance and cross-resistance.

In addition to the above growth promoters also used in therapy the so-called probiotics are more and more widespreadly applied. Probiotics are biologically active compositions which comprise the live or killed cultures of bacteria or other microorganisms occurring in animal or human organism. Probiotics exhibit their biological effect by colonization or modifying the pH-value absorption capacity of the gastro-intestinal flora. As compositions of this type e.g. the dried culture of hemiascomycetes and the liophylized life culture of *Streptococcus faecium* can be mentioned. Although probiotics are capable of eliminating the disadvantageous properties of antibiotics, their use is accompanied by several drawbacks. Thus their oral administration is complicated, their effect is uncertain (life microorganisms) and their activity is lower than that of other compositions used for this purpose.

The present invention is based on the recognition that prenylamine [N-(3'-phenyl-2'-propyl)-1,1-diphenyl-3-propyl-amine] and salts thereof, suitable for feeding purposes, when administered in a suitable dose exhibit a favourable effect on the microflora of the intestinal tract of the animals, regulate the absorption of nutriments and thus result in a significant increase of weight gain and improvement of fodder utilization.

According to an aspect of the present invention there are provided growth-promoter fodders or feed additives, comprising as active ingredient 0.002 to 98% by weight of prenylamine or a salt thereof, suitable for feeding purposes, in admixture with 99.988 to 2% by weight of an inert fodder carrier and optionally with further feed additives.

According to a further aspect of the present invention there is provided a process for the preparation of growth-promoter fodders or feed additives which comprises admixing 0.002 to 98% by weight or prenylamine or a salt thereof, suitable for feeding purposes, as active ingredient with inert fodder carriers and optionally with further feed additives.

The compositions of the present invention comprise preferably 45 to 55% by weight of prenylamine or a salt thereof.

As salt of prenylamine suitable for feeding purposes preferably the lactate, fumarate, tartarate, hydrochloride or sulphate of prenylamine can be used.

As carrier preferably grist of cereals (e.g. grist of maize, corn, wheat, barley, oat, rise or sorghum), or industrially processed products thereof, grist of leguminous plants or grits of oil industry (e.g. pea, bean, lupine, soya, rape, flax-seed, cotton-seed, broad-bean or sunflower seed) or grits of food-industry products or by-products (preferably dried grist of turnip slices, starch, yeast, powdered milk or whey, glutene, glutine or bone meal) or further industrial products (e.g. fodder lime, phosphates, perlite, furfural meal, cellulose meal or clay) can be used.

As biologically active further additives vitamin A, vitamin $B_1$, vitamin $B_2$, vitamin $B_3$, vitamin $B_6$, vitamin $B_{12}$, vitamin $D_3$, vitamin E, choline chloride, nicotinic acid, nicotinic amide, DL-methionine, L-lysine or cysteine or drugs or pharmaceutically active ingredients (e.g. zinc bacitracin, carbadox, furazolidon, salinomycin, virginiamycin, spiramycin, flavomycin, oxytetracycline, dimetridazole, or sulfaquinoxaline) can be used.

As feed-additives animal or vegetable fats or oils (e.g. hog-fat, lard, tallow, soya oil or lecithins) or antioxidants [e.g. butyl-hydroxy-toluene (BHT) or ethylmethoxy quinoline (EMQ)] can be applied as well.

As further feed-additives flavourants aroma substances, trace elements and macro elements can be used. As flavourants e.g. saccharine, vanilline and various sugars can be used. As aroma substances e.g. aroma substances and extracts of vegetable origin, cinnamon and camomile oil can be applied.

The trace elements or sources thereof may be copper sulphate or other copper salts, zinc sulphate or other zinc salts, cobalt sulphate or other cobalt salts, magnesium oxide, iron salts, manganese oxide, calcium iodate or selenium salts.

As macro elements or sources thereof preferably sodium chloride or calcium carbonate may be used.

The main advantages of the growth promoter fodder and feed additives of the present invention are as follows:

(a) significant weight gain increase;
(b) improved fodder utilization, i.e. the same amount of fodder results in a higher weight gain;
(c) preferable effect on the microflora of the intestinal tract, regulation of absorption of nutriments and consequently improved digestion;
(d) increase of the vitality and viability of the animals;
(e) the fodders and feed additives of the present invention are atoxical, not teratogenous and not carcinogenic;
(f) the fodders and feed additives of the present invention do not cause resistance;
(g) the fodders and feed additives of the present invention are compatible with any fodder, can be simply used and readily admixed with other components.
(h) the fodders and feed additives of the present invention are rapidly decomposed in animal organism and—contrary to antibiotics—do not cause problems connected with residues.

Further details of the present invention are to be found in the following Examples without limiting the scope of the invention to the said Examples.

EXAMPLE 1

0.1% by weight of prenylamine fumarate is admixed with 99.9% of maize flour in a countercurrent flash mixer (manufacturer ÉLGÉP). After 5 minutes of stirring a homogeneous product is obtained which can be very advantageously used as growth promoter of pigs.

EXAMPLE 2

2% by weight of prenylamine lactate are admixed with 98% by weight of wheat bran in the apparatus according to Example 1, whereupon 0.2% by weight of butyl hydroxy toluene is added.

The growth promoter fodder thus obtained can be very advantageously used for the increase of weight gain of pigs and cattle.

EXAMPLE 3

In the apparatus according to Example 1 20% by weight of prenylamine chloride are admixed with 78% of dried turnip slices and 2% of fodder lime. The homogenized product is packed in lots of 30 kg.

The feed additive thus obtained can be admixed with optional fodder and the mixture gives a significant weight-gain increase of cattle.

EXAMPLE 4

In the apparatus according to Example 1 75% by weight of prenylamine are admixed with 24% by weight of wheat bran, 1% of sodium saccharate, 15,000,000 IU of vitamin A, 3,000,000 IU of vitamin $D_3$ and 20,000 IU of vitamin E.

The feed additive thus obtained can be preferably used for the weight-gain increase of piglets in a concentration of 1 kg feed additive/1 t piglet fodder.

EXAMPLE 5

In the apparatus according to Example 1 98 parts by weight of prenylamine are admixed with 25 parts by weight of furfural flour, 20,000,000 IU of vitamin A and 4,000,000 IU of vitamin $D_3$.

0.5 kg of the feed additive thus obtained is added to 1 t of chicken starting feed.

The following feeding tests are carried out by using the composition of the present invention.

(A) Piglet Breeding Test

Comparative feeding tests are carried out on piglets weighing 8–30 kg, under identical group and breeding conditions, in four repetitions, by using 105 animals in each repetition, the total number of piglets being 420.

In this test the composition according to Example 2 is admixed with the fodder composition according to Table I in a concentration of 0.5% by weight. Thus the prenylamine concentration of the ready-for-use fodder amounts to 100 ppm/kg.

TABLE I

| Composition of fodder | Composition of piglet fodder | | |
|---|---|---|---|
| | Positive control group | Negative control group | Group according to the present invention |
| | % by weight | | |
| Cereals | 42.0 | 42.0 | 41.5 |
| Maize-germ | 10.0 | 10.0 | 10.0 |
| Fatless milk-powder | 15.0 | 15.0 | 15.0 |
| Extracted soya grits | 15.0 | 15.0 | 15.0 |
| Fish meal | 5.0 | 5.0 | 5.0 |
| Dextrine | 5.0 | 5.0 | 5.0 |
| Powdered fat (fat-content 50% by weight on a maize-flake carrier) | 5.0 | 5.0 | 5.0 |
| Dicalcium phosphate | 2.0 | 2.0 | 2.0 |
| Premix* | 1.0 | 1.0 | 1.0 |
| Composition according to Example 1 | — | — | 0.5 |
| Total: | 100.0 | 100.0 | 100.0 |

*The composition of the premix is disclosed in Table II.

The guaranteed internal value of 1 kg of the above fodder is as follows:
starch value=806 g/kg;
crude fat=at least 3%;

crude protein = at least 22.7%;
crude fibre = 1.7%.

The positive control group is fed with the premix having the composition according to Table II. The negative control group and the experimental group received premix containing no zinc bacitracin.

TABLE II

| Composition of premix | | | |
|---|---|---|---|
| Component | | Piglets | Young pigs |
| Vitamin A | IU | 1,000,000 | 3,000,000 |
| Vitamin $D_3$ | IU | 200,000 | 600,000 |
| Vitamin E | IU | 2,000 | 4,000 |
| Vitamin $B_2$ | IU | 400 | 400 |
| Vitamin $B_3$ | IU | 2,000 | 2,000 |
| Vitamin $B_{12}$ | IU | 5 | 5 |
| Niacin | | 2,400 | 2,400 |
| Choline chloride | | 40,000 | 40,000 |
| Zinc bacitracin | | 3,000 | 3,000 |
| BHT | | 30,000 | 30,000 |
| $Mn^{2+}$ | | 6,000 | 6,000 |
| $Fe^{2+}$ | | 10,000 | 10,000 |
| $Zn^{2+}$ | | 15,000 | 15,000 |
| $Cu^{2+}$ | | 30,000 | 30,000 |
| $J^-$ | | 100 | 100 |
| Twice ground bran ad g | | 1,000 | 1,000 |

The premix of the positive control contains 0.25 g of Bayo-Nox/kg premix.

According to the experimental results registered and evaluated during the piglet breeding period in the group fed with a fodder comprising prenylamine the number of dysenteric diseases of the piglets decrease, the loss of piglets is reduced, the specific fodder utilization and average daily weight gain are significantly increased as related to both the positive and negative control groups. The results are summarized in the following Table III.

TABLE III

| | Positive control group | Negative control group | Experimental group |
|---|---|---|---|
| Number of days on which diarrhoea occured | 224 | 360 | 136 |
| Losses on piglets (death, emergency slaughter, sorting out) % | 10 | 15.71 | 7.14 |
| Weight gain (average daily g/animal) | 370 | 342 | 389 |
| Specific fodder utilization (kg of fodder/kg weight gain) | 2.53 | 2.78 | 2.40 |

In the two replicates the trend of the experimental results is completely identical and for this reason in the above Table III the total results of both replicates are disclosed (420 piglets).

(B) Pig Breeding Test

Comparative pig feeding tests are carried out on pigs weighing 30 to 120 kg under identical breeding, genetic and feeding conditions, in two repetitions. In each repetition 150 porkers (totally 300 animals) are used.

In this test 0.25% by weight of the composition according to Example 2 is admixed with the fodder composition disclosed in Table IV. Thus 1 kg of ready-for-use fodder comprises 50 ppm of prenylamine.

TABLE IV

| Component | Positive control group | Negative control group | Experimental group |
|---|---|---|---|
| | % by weight | | |
| Maize | 62 | 62 | 61.75 |
| Wheat | 14.2 | 14.2 | 14.2 |
| Barley | 8 | 8 | 8 |
| Bran | 4 | 4 | 4 |
| Alfalfa meal | 2 | 2 | 2 |
| Meat meal | 5 | 5 | 5 |
| Powdered fat (50%) | 1.5 | 1.5 | 1.5 |
| Fodder lime | 1.1 | 1.1 | 1.1 |
| Mineral premix containing 17% of P | 1.3 | 1.3 | 1.3 |
| Premix 17 | 0.5 | — | — |
| Premix 17 containing no zinc bacitracin | — | 0.5 | 0.5 |
| Composition according to Example 2 | — | — | 0.25 |
| Fodder salt | 0.4 | 0.4 | 0.4 |

It can be seen from the registered and evaluated feeding data that in the group which had received prenylamine the loss of porkers decreased, weight gain increased and fodder utilization improved. The results are summarized in Table V.

TABLE V

| | Positive control group | Negative control group | Experimental group |
|---|---|---|---|
| Losses (death, emergency slaughter, sorting out) | 11 | 15 | 8 |
| Average daily weight gain g/day/animal | 577 | 542 | 590 |
| Specific fodder utilization kg/fodder/kg weight gain | 3.80 | 4.12 | 3.68 |

The trends of the experimental results are identical in both repetitions and for this reason in Table V the common results of both repetitions are disclosed. Thus three times 100 (300) animals are used.

What we claim is:
1. A method of promoting the growth of an animal which comprises feeding a small but effective amount of prenylamine or a salt thereof, suitable for feeding purposes, to said animal.
2. The method of claim 1, wherein the prenylamine or its salt is pre-mixed with an inert fodder carrier and optionally with further feed additives.
3. The method of claim 1, wherein the animals are pigs.
4. The method of claim 1, wherein the animals are cattle.
5. The method of claim 1, wherein the animals are poultry.
6. The method of claim 5, wherein the poultry are chickens.

* * * * *